United States Patent
Aizawa et al.

(10) Patent No.: US 10,442,768 B2
(45) Date of Patent: Oct. 15, 2019

(54) METHOD FOR PRODUCING 2-AMINONICOTINIC ACID BENZYL ESTER DERIVATIVE

(71) Applicant: AGRO-KANESHO CO., LTD., Minato-ku (JP)

(72) Inventors: Ryo Aizawa, Tokorozawa (JP); Koichi Araki, Ushiku (JP)

(73) Assignee: AGRO-KANESHO CO., LTD., Minato-ku (JP)

( * ) Notice: Subject to any disclaimer, the term of this patent is extended or adjusted under 35 U.S.C. 154(b) by 0 days.

(21) Appl. No.: 15/781,302

(22) PCT Filed: Nov. 8, 2016

(86) PCT No.: PCT/JP2016/083100
§ 371 (c)(1),
(2) Date: Jun. 4, 2018

(87) PCT Pub. No.: WO2017/126197
PCT Pub. Date: Jul. 27, 2017

(65) Prior Publication Data
US 2018/0362464 A1 Dec. 20, 2018

(30) Foreign Application Priority Data
Jan. 21, 2016 (JP) .................. 2016-009963

(51) Int. Cl.
| | | |
|---|---|---|
| *C07D 213/803* | (2006.01) | |
| *C07D 213/80* | (2006.01) | |
| *C07D 401/12* | (2006.01) | |
| *C07B 61/00* | (2006.01) | |

(52) U.S. Cl.
CPC ....... *C07D 213/803* (2013.01); *C07D 213/80* (2013.01); *C07D 401/12* (2013.01); *C07B 61/00* (2013.01)

(58) Field of Classification Search
CPC . C07D 213/80; C07D 213/803; C07D 401/12
See application file for complete search history.

(56) References Cited

U.S. PATENT DOCUMENTS

| 6,200,999 B1 | 3/2001 | Bang-Andersen et al. |
| 2016/0318868 A1 | 11/2016 | Aizawa et al. |

FOREIGN PATENT DOCUMENTS

| JP | 4-108793 A | | 4/1992 |
| JP | 2001-501630 A | | 2/2001 |
| JP | 2015-30693 A | | 2/2015 |
| JP | 2015-120675 A | | 7/2015 |
| WO | 2015097850 | * | 7/2015 |
| WO | WO 2015/097850 A1 | | 7/2015 |

OTHER PUBLICATIONS

International Search Report dated Jan. 24, 2017 in PCT/JP2016/083100 filed Nov. 8, 2016.
K. Mori et al., "Selective Activation of Enantiotopic C(sp$^3$)—Hydrogen by Means of Chiral Phosphoric Acid: Asymmetric Synthesis of Tetrahydroquinoline Derivatives", Journal of the American Chemical Society, Apr. 5, 2011, vol. 133, 41 total pages.
Combine Russian Federation Office Action and Search Report dated Apr. 12, 2019 in Patent Application No. 2018130080/04(048715) (with English translation), 12 pages.

* cited by examiner

*Primary Examiner* — D Margaret M Seaman
(74) *Attorney, Agent, or Firm* — Oblon, McClelland, Maier & Neustadt, L.L.P.

(57) ABSTRACT

The present invention provides a method for producing a 2-aminonicotinic acid benzyl ester derivative. The method includes, as a step, reacting a 2-aminonicotinic acid derivative represented by the formula [I], wherein $R^1$ represents a hydrogen atom or a $C_1$ to $C_4$ alkyl group and M represents an alkali metal, with a benzyl derivative represented by the formula [II], wherein $R^2$ represents, for example, a hydrogen atom or a halogen atom, A represents, for example, a nitrogen atom, X represents a halogen atom, and Y represents, for example, an oxygen atom, in an aromatic hydrocarbon solvent in the presence of a phase transfer catalyst or a tertiary amine.

3 Claims, No Drawings

METHOD FOR PRODUCING 2-AMINONICOTINIC ACID BENZYL ESTER DERIVATIVE

TECHNICAL FIELD

The present invention relates to a method for producing a 2-aminonicotinic acid benzyl ester derivative. Specifically, the present invention relates to an industrial production method for producing a 2-aminonicotinic acid benzyl ester derivative which is a useful compound as an effective component of an agricultural fungicide in a high yield at a high purity with a high volume efficiency and little effect on the environment.

BACKGROUND ART

As general methods for producing an ester derivative, there have been known a method comprising chlorinating a carboxylic acid derivative by using a halogenating agent and reacting the resultant product with an alcohol derivative in an organic solvent in the presence of abase, a method comprising reacting a carboxylic acid derivative with an alcohol derivative in an organic solvent by using a condensing agent, and similar methods.

As a method for producing a 2-aminonicotinic acid ester derivative, Patent Literature 1 discloses a method for producing a 2-aminonicotinic acid ester derivative represented by the following reaction formula:

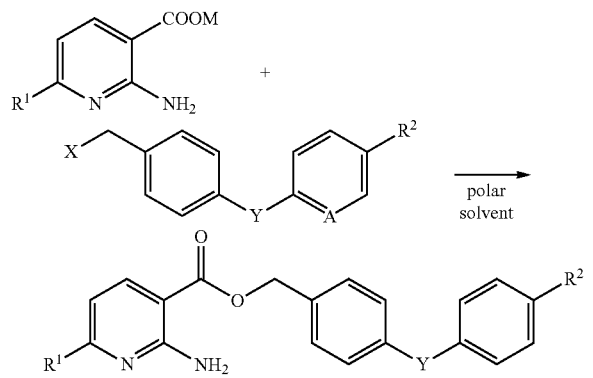

wherein M is an alkali metal and X is a halogen atom.

Although the aforementioned method of Patent Literature 1 can produce a 2-aminonicotinic acid ester derivative in a high yield at a high purity, the viscosity of the reaction solution tends to be high and it is difficult to achieve a volume efficiency of 10% or more in production. Moreover, since a water-soluble polar solvent is used, it is impossible to eliminate concerns about environmental load in solvent recycle and waste liquid treatment after the reaction.

CITATION LIST

Patent Literature

Patent Literature 1: WO2015/097850

SUMMARY OF INVENTION

Problem to be Solved by the Invention

Patent Literature 1 states that, in a conventional technique, a general method for producing an ester derivative is not preferable for production of a 2-aminonicotinic acid ester derivative. Specifically, when a 2-aminonicotinic acid ester derivative is chlorinated, the reaction solution turns brown. In this case, the intended reaction is hindered and the amount of by-products increases. Moreover, the reaction is not completed even by using a condensing agent. Furthermore, the method described in Patent Literature 1 is not necessarily an optimal production method due to low volume efficiency and effect on the environment. Accordingly, there is a demand for development of an industrial production method for producing a target substance in a high yield at a high purity and for achieving a high volume efficiency with little effect on the environment.

Means for Solving the Problem

The present inventors earnestly studied to solve the problems described above and, as a result, found a method comprising reacting a 2-aminonicotinic acid derivative with a benzyl derivative at a high concentration by using an aromatic hydrocarbon solvent in the presence of a phase transfer catalyst or a catalyst quantity of a tertiary amine, and arrived at the present invention.

Specifically, the present invention provides a method for producing a 2-aminonicotinic acid benzyl ester derivative, comprising:

reacting a 2-aminonicotinic acid derivative represented by the following formula [I]:

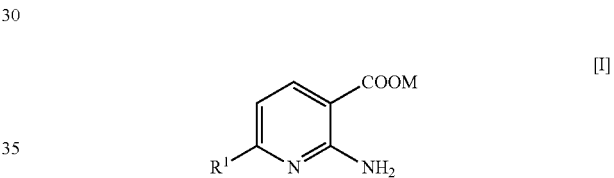

wherein $R^1$ represents a hydrogen atom or a $C_1$ to $C_4$ alkyl group and M represents a hydrogen atom or an alkali metal, with a benzyl derivative represented by the following formula [II]:

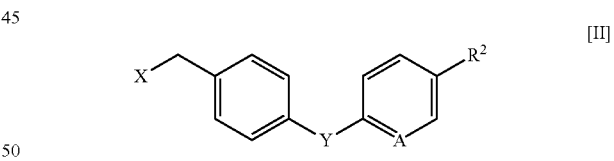

wherein $R^2$ represents a hydrogen atom, a halogen atom, a $C_1$ to $C_4$ alkyl group or a $C_1$ to $C_4$ alkoxy group; A represents a nitrogen atom or a methine group (CH); X represents a hydroxyl group or a halogen atom; and Y represents an oxygen atom, a methylene group ($CH_2$) or a methyleneoxy group ($OCH_2$), a) by using a base when M is a hydrogen atom in the formula [I], and b) by using an halogenating agent when X is a hydroxyl group in the formula [II], and then reacting the 2-aminonicotinic acid derivative with the benzyl derivative in an aromatic hydrocarbon solvent in the presence of a phase transfer catalyst or a tertiary amine, so as to produce a 2-aminonicotinic acid benzyl ester derivative represented by the following formula [III]:

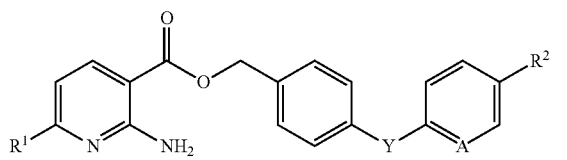

wherein $R^1$, $R^2$, A and Y are as defined in the formulae [I] and [II].

Effect by the Invention

According to the present production method, it is expected that a 2-aminonicotinic acid benzyl ester derivative is prepared in a high yield, while a higher volume efficiency and a lower environmental load than those in a conventional technique are achieved. Specifically, using an aromatic hydrocarbon solvent as a poor solvent can suppress an increase in viscosity even for a high-concentration slurry and maintain stirrability, compared to the case of using the polar solvent. This improves the productivity when the same production apparatus is used. Moreover, since an aromatic hydrocarbon solvent can be easily reused, the present invention is effective in reducing the environmental load.

DESCRIPTION OF EMBODIMENT OF THE INVENTION

The present invention is described below in detail.

In the formulae [I], [II], and [III] described above, the $C_1$ to $C_4$ alkyl group represented by $R^1$ and $R^2$ includes a methyl group, an ethyl group, an n-propyl group, an isopropyl group, an n-butyl group, an isobutyl group, a sec-butyl group, a tert-butyl group and the like; the halogen atom represented by $R^2$ and X includes a fluorine atom, a chlorine atom, a bromine atom and an iodine atom; the $C_1$ to $C_4$ alkoxy group represented by $R^2$ includes a methoxy group, an ethoxy group, an n-propoxy group, an isopropoxy group, an n-butoxy group, an isobutoxy group, a sec-butoxy group and a tert-butoxy group; and the alkali metal represented by M includes sodium and potassium.

The production method of the present invention may comprise steps of: when M in the aforementioned formula [I] is hydrogen, adding a base such as an alkali metal hydroxide, e.g., sodium hydroxide or potassium hydroxide, an alkali metal carbonate such as sodium carbonate or potassium carbonate, or the like in an amount of, for example, 1 to 10 times by mole, preferably 1 to 5 times by mole, relative to the aforementioned formula [I], in an aromatic hydrocarbon solvent such as benzene, toluene or xylene, followed by stirring, for example, for 1 minute to 1 hour at 0 to 100° C., preferably for 5 to 30 minutes at 20 to 60° C.; and when X in the aforementioned formula [II] is a hydroxyl group, adding a halogenating agent such as thionyl chloride, thionyl bromide or phosphorus oxychloride in an amount of, for example, 1.0 to 3.0 times by mole, preferably 1.0 to 1.5 times by mole, relative to the compound of the aforementioned formula [II], in an aromatic hydrocarbon solvent such as benzene, toluene or xylene, followed by stirring, for example for 5 minutes to 1 hour at −5 to 30° C., preferably for 10 to 40 minutes at 0 to 25° C. After the aforementioned processing is performed as necessary, the compounds of the aforementioned formulae [I] and [II] are mixed in an aromatic hydrocarbon solvent such as benzene, toluene or xylene, and then a phase transfer catalyst such as tetrabutylammonium chloride, tetrabutylammonium bromide, tetrabutylammonium iodide, benzyltriethylammonium bromide, 15-crown-5 ether or 18-crown-6 ether or a tertiary amine such as trimethylamine, triethylamine, dimethylisopropylamine, tetramethylethylenediamine or 1,4-diazabicyclo[2,2,2]octane is added in an amount of, for example, 0.001 to 0.1 times by mole, preferably 0.005 to 0.05 times by mole, relative to the compound of the aforementioned formula [I], followed by stirring for 5 minutes to 10 hours at 0 to 130° C., preferably for 2 to 6 hours at 70 to 120° C. After the reaction, the reaction solution is distilled under reduced pressure to evaporate, for example, 10 to 100% of organic solvent. Ice water is poured into the reaction solution, followed by stirring, for example, for 5 to 30 minutes, preferably for 10 to 20 minutes and a precipitated crystal is collected by filtration and dried. Thereby, the compound of the aforementioned formula [III] as a target compound can be very easily obtained in a high yield at a high purity. Moreover, it is only sufficient to use an aromatic hydrocarbon solvent in an amount, for example, 3 to 5 times the maximum amount of the theoretical value of the target compound obtainable, and a volume efficiency is as high as about 20 to 35%. Furthermore, the aromatic hydrocarbon solvent can be easily separated from water by distilling the reaction solution or filtrate under reduced pressure and be reused thereby to reduce environmental burden.

In the production method of the present invention, the aromatic hydrocarbon solvent used in the reaction between the alkali metal hydroxide and the compound of the aforementioned formula [I] wherein M in the formula [I] is a hydrogen atom and the aromatic hydrocarbon solvent used in the reaction between the halogenating agent and the compound of the aforementioned formula [II] may be the same or different, but are preferably the same.

The nicotinic acid derivative represented by the aforementioned formula [I], which is used in the production method of the present invention, can be readily synthesized from a publicly-known compound according to, for example, a method described in JP-A-2010-083861.

The alcohol derivative represented by the aforementioned formula [II] where X is a hydroxyl group, which is used in the production method of the present invention, can be readily synthesized from a publicly-known compound according to, for example, a method described in Journal of Medicinal Chemistry, vol. 43, p. 1826 (2000).

The compound of the aforementioned formula [III] which is produced in the production method of the present invention is useful as an agricultural fungicide.

EXAMPLES

The present invention will be further described below by reference to Examples, but the scope of the present invention is not at all limited to the following Examples.

Example 1

Synthesis of 2-amino-6-methylnicotinic acid-4-phenoxybenzyl

First, potassium 2-amino-6-methylnicotinate (0.95 g) was suspended in toluene (5 mL), and (1-chloromethyl)-4-phenoxybenzene (1.10 g) and 18-crown-6 ether (40 mg) were added thereto, followed by stirring under heating for 6 hours at 105° C. The reaction solution was cooled to room temperature and about 80% of toluene was evaporated under reduced pressure. Ice water was added to the residue, followed by stirring for 20 minutes at room temperature. The precipitated crystal was collected by filtration and dried and 1.52 g (yield of 91.6%, volume efficiency of 33.4%) of the target substance (compound 2 described in Table 1) was obtained.

$^1$H-NMR (CDCl$_3$) δ ppm: 2.38 (3H, s), 5.25 (2H, s), 6.06-6.72 (2H. br), 6.44 (1H, d), 6.99-7.04 (4H, m), 7.12 (1H, t), 7.31-7.41 (4H, m), 8.04 (1H, d)

Example 2

Synthesis of 2-amino-6-methylnicotinic acid-4-phenoxybenzyl

First, potassium 2-amino-6-methylnicotinate (0.95 g) was suspended in m-xylene (5 mL), and (1-chloromethyl)-4-phenoxybenzene (1.10 g) and tetramethylethylenediamine (19 mg) were added thereto, followed by stirring under heating for 6 hours at 110° C. The reaction solution was cooled to room temperature and about 80% of m-xylene was evaporated under reduced pressure. Ice water was added to the residue, followed by stirring for 20 minutes at room temperature. The precipitated crystal was collected by filtration and dried and 1.41 g (yield of 84.4%, volume efficiency of 33.4%) of the target substance (compound 2 described in Table 1) was obtained.

Example 3

Synthesis of 2-amino-6-methylnicotinic acid-4-phenoxybenzyl

First, potassium 2-amino-6-methylnicotinate (0.95 g) was suspended in m-xylene (5 mL), and (1-chloromethyl)-4-phenoxybenzene (1.10 g) and tetrabutylammoniumbromide (49 mg) were added thereto, followed by stirring under heating for 6 hours at 110° C. The reaction solution was cooled to room temperature and about 90% of m-xylene was evaporated under reduced pressure. Ice water was added to the residue, followed by stirring for 20 minutes at room temperature. The precipitated crystal was collected by filtration and dried and 1.55 g (yield of 92.8%, volume efficiency of 33.4%) of the target substance (compound 2 described in Table 1) was obtained.

Example 4

Synthesis of 2-amino-6-methylnicotinic acid-4-phenoxybenzyl

First, 2-amino-6-methylnicotinic acid (2.28 g) was suspended in m-xylene (15 mL), and sodium hydroxide (1.20 g) was added thereto, followed by stirring for 30 minutes at 40° C. to obtain Solution 1. On the other hand, (4-phenoxyphenyl)methanol (3.00 g) was dissolved in m-xylene (5 mL), thionyl chloride (1.1 mL) was added dropwise at ice-cold temperature, followed by stirring for 30 minutes while returning to room temperature. Then, Solution 1 was added to this reaction solution, tetrabutylammoniumbromide (145 mg) was added thereto, followed by stirring under heating for 6 hours at 110° C. The reaction solution was cooled to room temperature and about 90% of m-xylene was evaporated under reduced pressure. Ice water was added to the residue, followed by stirring for 30 minutes at room temperature. The precipitated crystal was collected by filtration and dried and 4.17 g (yield of 83.2%, volume efficiency of 20%) of the target substance (compound 2 described in Table 1) was obtained.

Example 5

Synthesis of 2-amino-6-methylnicotinic acid-4-phenoxybenzyl

First, 2-amino-6-methylnicotinic acid (3.04 g) was suspended in m-xylene (20 mL), potassium carbonate (4.15 g) was added thereto, followed by stirring for 30 minutes at 40° C. to obtain Solution 1. On the other hand, (4-phenoxyphenyl)methanol (4.00 g) was dissolved in m-xylene (7 mL), thionyl chloride (1.46 mL) was added dropwise at ice-cold temperature, followed by stirring for 30 minutes while returning to the room temperature. Then, hydrogen chloride, sulfur dioxide and thionyl chloride in the system were evaporated, Solution 1 was added, tetrabutylammonium bromide (194 mg) was added, followed by stirring under heating for 4 hours at 110° C. The reaction solution was cooled to room temperature and about 95% of m-xylene was evaporated under reduced pressure. Ice water was added to the residue, followed by stirring for 30 minutes at room temperature. The precipitated crystal was collected by filtration and dried and 6.39 g (yield of 95.7%, volume efficiency of 25%) of the target substance (compound 2 described in Table 1) was obtained.

Table 1 below provides the data on not only Compound 2 of the present invention but also Compounds 1 and 3 to 8 of the present invention which were produced in the same method as Example 1.

TABLE 1

[IV]

| Compound No. | $R^1$ | $R^2$ | A | Y | mp (° C.) | Yield (%) |
|---|---|---|---|---|---|---|
| 1 | H | H | CH | O | 116-118 | 93.9 |
| 2 | CH$_3$ | H | CH | O | 122-124 | 95.7 |
| 3 | CH$_3$ | F | CH | O | 104-106 | 91.1 |
| 4 | CH$_3$ | CH$_3$ | CH | O | 94-96 | 94.0 |
| 5 | CH$_3$ | OCH$_3$ | CH | O | 107-109 | 92.8 |
| 6 | CH$_3$ | H | N | O | 120-121 | 86.9 |
| 7 | CH$_3$ | H | CH | OCH$_2$ | 140-142 | 90.7 |
| 8 | CH$_3$ | H | CH | CH$_2$ | 106-108 | 88.5 |

As described above, the present production method is a method of a high industrial value, producing a 2-aminonicotinic acid benzyl ester derivative as an agricultural fungicide.

What is claimed is:

1. A method for producing a 2-aminonicotinic acid benzyl ester derivative of formula (III), comprising:

reacting a 2-aminonicotinic acid derivative represented by the following formula [I]:

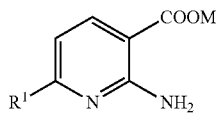

wherein R¹ represents a hydrogen atom or a $C_1$ to $C_4$ alkyl group and M represents a hydrogen atom or an alkali metal, and a benzyl derivative represented by the following formula [II]:

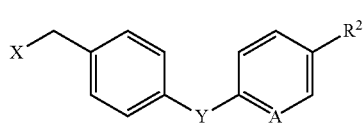

wherein $R^2$ represents a hydrogen atom, a halogen atom, a $C_1$ to $C_4$ alkyl group or a $C_1$ to $C_4$ alkoxy group, A represents a nitrogen atom or a methine group (CH), X represents a hydroxyl group or a halogen atom, and Y represents an oxygen atom, a methylene group ($CH_2$) or a methyleneoxy group ($OCH_2$), a) by using a base when M is a hydrogen atom in the formula [I], and b) by using an halogenating agent when X is a hydroxyl group in the formula [II], and then reacting the 2-aminonicotinic acid derivative with the benzyl derivative in an aromatic hydrocarbon solvent in the presence of a phase transfer catalyst or a tertiary amine, to produce a 2-aminonicotinic acid benzyl ester derivative represented by the following formula [III]:

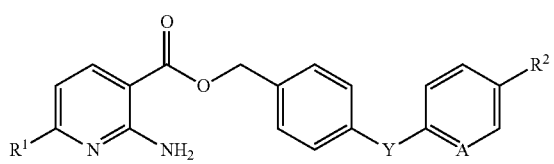

wherein $R^1$, $R^2$, A and Y are as defined in the formulae [I] and [II].

2. A method for producing a 2-aminonicotinic acid benzyl ester derivative of formula (III), comprising:

reacting a 2-aminonicotinic acid inorganic salt derivative represented by the following formula [IV]:

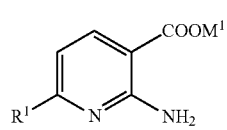

wherein $R^1$ represents a hydrogen atom or a $C_1$ to $C_4$ alkyl group and $M^1$ represents an alkali metal, with a benzyl halide derivative represented by the following formula [V]:

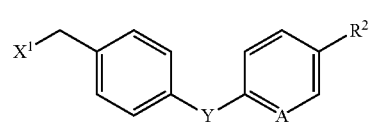

wherein $R^2$ represents a hydrogen atom, a halogen atom, a $C_1$ to $C_4$ alkyl group or a $C_1$ to $C_4$ alkoxy group, A represents a nitrogen atom or a methine group (CH), $X^1$ represents a halogen atom, and Y represents an oxygen atom, a methylene group ($CH_2$) or a methyleneoxy group (OCH), in an aromatic hydrocarbon solvent in the presence of a phase transfer catalyst or a tertiary amine, to produce a 2-aminonicotinic acid benzyl ester derivative represented by the following formula [III]:

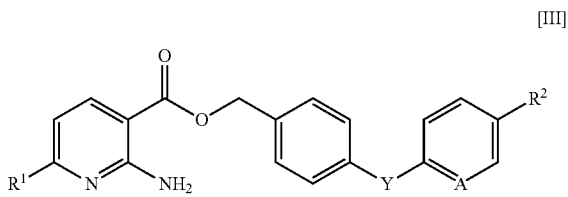

wherein $R^1$, $R^2$, A and Y are as defined in the formulae [IV] and [V].

3. A method for producing a 2-aminonicotinic acid benzyl ester derivative of formula (III), comprising:

reacting a 2-aminonicotinic acid derivative represented by the following formula [VI]:

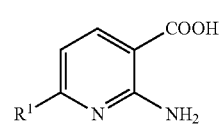

wherein $R^1$ represents a hydrogen atom or a $C_1$ to $C_4$ alkyl group, with a compound obtained by reacting, with a halogenating agent, a benzyl alcohol derivative represented by the following formula [VII]:

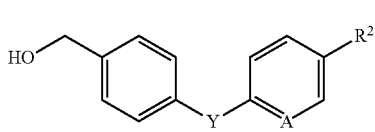

wherein $R^2$ represents a hydrogen atom, a halogen atom, a $C_1$ to $C_4$ alkyl group or a $C_1$ to $C_4$ alkoxy group, A represents a nitrogen atom or a methine group (CH), and Y represents an oxygen atom, a methylene group ($CH_2$) or a methyleneoxy group ($OCH_2$), that is, a benzyl halide derivative represented by the following formula [II]:

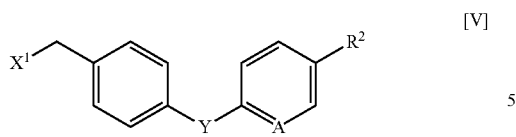

[V]

wherein $R^2$, A and Y are as defined in the formula [VII] and $X^1$ represents a halogen atom, in an aromatic hydrocarbon solvent in the presence of a base and a phase transfer catalyst or a tertiary amine, to produce a 2-aminonicotinic acid benzyl ester derivative represented by the following formula [III]:

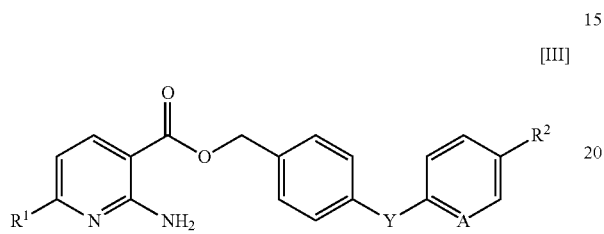

[III]

wherein $R^1$, $R^2$, A and Y are as defined in the formulae [VI] and [VII].

* * * * *